United States Patent
Ohlstein

Patent Number: 5,453,436
Date of Patent: Sep. 26, 1995

[54] TREATMENT OF ATHEREOSCLEROSIS USING, CARBAZOLYL-(4)-OXYPROPANOLAMINE COMPOUNDS

[75] Inventor: Eliot H. Ohlstein, Glenmoore, Pa.

[73] Assignees: Boehringer Mannheim Pharmaceutical Corporation; SmithKline Beecham Corp., both of Rockville, Md.

[21] Appl. No.: 197,645

[22] Filed: Mar. 17, 1994

Related U.S. Application Data

[62] Division of Ser. No. 26,892, Mar. 5, 1993, Pat. No. 5,308,862.

[51] Int. Cl.$^6$ .................................................. A61K 31/40
[52] U.S. Cl. ............................................................ 514/411
[58] Field of Search ............................................... 514/411

[56] References Cited

U.S. PATENT DOCUMENTS 4,503,067   3/1985   Wiedemann et al. .................. 514/411

OTHER PUBLICATIONS

Stedman's Medical Dictionary, Twenty-second Edition, Williams & Wilkins Co., Baltimore, Md., (1972) p. 123.

Primary Examiner—Marianne M. Cintins
Assistant Examiner—T. J. Criares
Attorney, Agent, or Firm—Yuriy P. Stercho; Stuart R. Suter; Edward T. Lentz

[57] ABSTRACT

A new use of, and method of treatment of atherosclerosis using, a compound selected from the group consisting essentially of compounds of Formula I:

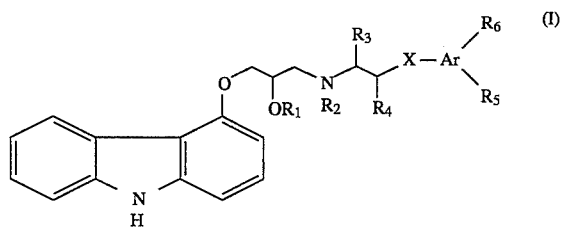

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkylsulphinyl of up to 6 carbon atoms and lower alkylsulphonyl of up to 6 carbon atoms; or $R_5$ and $R_6$ together represent methylenedioxy;

or a pharmaceutically acceptable salt thereof, for inhibition of proliferation of smooth muscle cells.

3 Claims, No Drawings

TREATMENT OF ATHEREOSCLEROSIS USING, CARBAZOLYL-(4)-OXYPROPANOLAMINE COMPOUNDS

This is a divisional of application Ser. No. 08/026,892, filed Mar. 5, 1993 now U.S. Pat. No. 5,308,862.

FIELD OF THE INVENTION

The present invention relates to a new medical use of the carbazolyl-(4)-oxypropanolamine compounds of Formula I, particularly carvedilol, for inhibiting proliferation of smooth muscle cells. In particular, the present invention provides a new use of carvedilol for making pharmaceutical compositions useful in prevention of restenosis following percutaneous transluminal coronary angioplasty (PTCA), for suppressing the progression of vascular hypertrophy associated with hypertension and prevention of development of atherosclerosis.

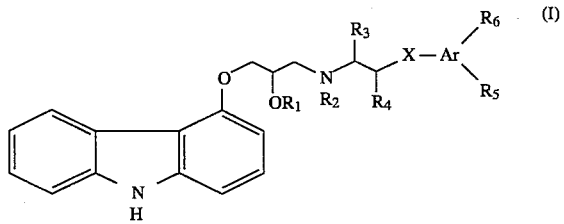

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy.

BACKGROUND OF THE INVENTION

Abnormal vascular smooth muscle proliferation is associated with cardiovascular disorders such as atherosclerosis, hypertension and most endovascular procedures. Abnormal vascular smooth muscle proliferation is a common complication of percutaneous transluminal coronary angioplasty (PTCA). The incidence of chronic restenosis resulting from vascular smooth muscle proliferation following PTCA has been reported to be as high as 40–45% within 3–6 months. Capron, L., Heudes, D., Chajara, A. & Bruneval, P. (1991) *J. Cardiovasc. Pharmacol.*, 18, 207–211; Bourassa, M. (1992) *J. Am. Coll. Cardiol.*, 19, 1410–1411. Several neurohumoral factors, including angiotensin II and norepinephrine, as well as growth factors, including platelet-derived growth factor (PDGF) and basic fibroblast growth factor (FGF), have been implicated in the development of vascular restenosis in vivo. Bourassa, M., et al. supra; Powell, J. S., Clozel, J.-P., Müller, R. K. M., Kuhn, H., Hefti, F., Hosang, M. & Baumgartner, H. R. (1989) *Science*, 245, 186–198; Clozel, J.-P., Hess, P., Michael, C., Schietinger, K. & Baumgartner, H. R. (1991) *Hypertension*, 18 (Suppl. II), II55–II59; Fingerle, J., Sanders, K. H. & Fotev, Z.( 1991 ) *Basic Res. Cardiol.*, 86, 75–81; Forney-Prescott, M., Webb, R. L. & Reidy, M. A. (1991) *Am. J. Pathol.*, 139, 1291–1296.; Kauffman, R. F., Bean, J. S., Zimmerman, K. M., Brown, R. F. & Steinberg, M. I. (1991 ) *Life Sci.*, 49, 223–228; Azuma, H., Y. & Hamasaki, H. (1992) *Br. J. Pharmacol.*, 106, 665–671.; Ferns, G. A. A., Raines, E. W., Sprugel, K. H., Motani, A. S., Reidy, M. A. & Ross, R. (1991 ) *Science*, 253, 1129–1132; and Lindner, V. & Reidy M. A. (1991) *Proc. Natl Acad. Sci.* (USA), 88 3739–3743.

The high incidence of vascular reocclusion associated with PTCA has led to the development of in vivo animal models of restenosis and the search for agents to prevent restenosis. Angiotensin II receptor antagonists, angiotensin convening enzyme (ACE) inhibitors, a-adrenoceptor antagonists and growth factor antibodies have generally produced only a modest (10–50%) reduction of vascular restenosis in such animal models. Powell, J. S., et al., supra; Fingerle, J., et al., supra; Forney-Prescott, M., et al., supra; and Kauffman, R. F., et al., supra. Clinical studies with ACE inhibitors (which showed only a slight protective effect in animal models of restenosis) have failed to demonstrate significant efficacy in the prevention of angiographically-defined restenosis in humans. Popma, J. J., Califf, R. M. & Topol, E. J. (1991) *Circulation*, 84, 1426–1436. This limited or insignificant protection against vascular restenosis afforded by agents with specific mechanisms of action most likely reflects the complex nature of the pathophysiology underlying vascular restenosis; a multiplicity of chemotactic and mitogenic factors are believed to be involved in this response to vascular wall injury, and it is unlikely that interfering with the actions of only one of these factors will prove to be beneficial.

Therefore, therapeutic anti-mitotic agents which reduce or prevent the abnormal proliferation of smooth muscle cells associated with cardiovascular disorders such as atherosclerosis and vascular hypertrophy associated with hypertension, or resulting from complications following PTCA and causing chronic restenosis are highly desirable.

SUMMARY OF THE INVENTION

In a first aspect, the present invention provides a new medical use for the carbazolyl-(4)-oxypropanolamine compounds of Formula I as anti-mitotic agents for inhibition of smooth muscle cell growth. In particular, the present invention preferably provides a new use for the compound of Formula I wherein $R_1$ is —H, $R_2$ is —H, $R_3$ is —H, $R_4$ is —H, X is O, Ar is phenyl, $R_5$ is ortho —$OCH_3$, and $R_6$ is —H, said compound being better known as carvedilol (1-(carbazol-4-yloxy-3-[[2-(o-methoxyphenoxy)ethyl] amino] -2-propanol), or a pharmaceutically acceptable salt thereof, said compound being used to make pharmaceutical compositions useful in prevention of restenosis following PTCA, for suppressing the progression of vascular hypertrophy associated with hypertension, and prevention of the development of atherosclerosis.

In a second aspect, the present invention also provides a method of treatment for prevention of restenosis following PTCA, for suppressing the progression of vascular hypertrophy associated with hypertension, and prevention of the development of atherosclerosis in mammals comprising internally administering to a mammal, preferably a human, in need thereof an effective amount of a compound selected from the group consisting essentially of the compounds of Formula I, preferably the compound of Formula I wherein $R^1$ is —H, $R^2$ is —H, $R^3$ is —H, $R^4$ is —H, X is O, Ar is phenyl, $R^5$ is ortho —$OCH_3$, and $R^6$ is —H, that is carvedilol, or a pharmaceutically acceptable salt thereof.

DETAILED DESCRIPTION OF THE INVENTION

U.S. Pat. No. 4,503,067 discloses carbazolyl-(4)-oxypropanolamine compounds of Formula I:

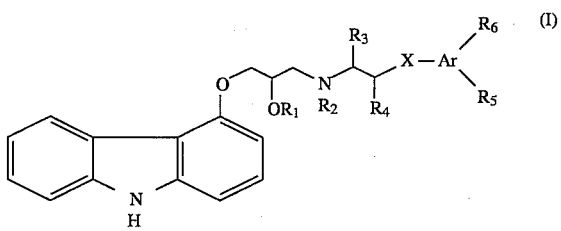

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy; and pharmaceutically acceptable salts thereof.

This patent further discloses a compound of Formula I, better known as carvedilol (1-(carbazol-4-yloxy-3-[[2-(o-methoxyphenoxy)ethyl]amino]-2-propanol), having the structure shown in Formula II:

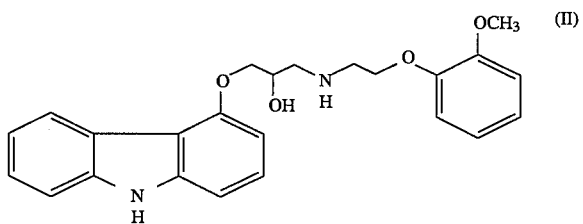

These compounds, of which carvedilol is exemplary, are novel multiple action drugs useful in the treatment of mild to moderate hypertension and having utility in angina and congestive heart failure (CHF). Carvedilol is known to be both a competitive b-adrenoceptor antagonist and a vasodilator, and is also a calcium channel antagonist at higher concentrations. The vasodilatory actions of carvedilol result primarily from $a_1$-adrenoceptor blockade, whereas the b-adrenoceptor blocking activity of the drug prevents reflex tachycardia when used in the treatment of hypertension. These multiple actions of carvedilol are responsible for the antihypertensive efficacy of the drug in animals, particularly in humans, as well as for utility in the treatment of angina and CHF. See Willette, R. N., Sauermelch, C. F. & Ruffolo, R. R., Jr. (1990) *Eur. J. Pharmacol.,* 176, 237–240; Nichols, A. J., Gellai, M. & Ruffolo, R. R., Jr. (1991) *Fundam. Clin. Pharmacol.,* 5, 25–38; Ruffolo, R. R., Jr., Gellai, M., Hieble, J. P., Willette, R. N. & Nichols, A. J. (1990) *Eur. J. Clin. Pharmacol.,* 38, S82–S88; Ruffolo, R. R., Jr., Boyle, D. A., Venuti, R. P. & Lukas, M. A. (1991) *Drugs of Today,* 27, 465–492; and Yue, T.-L., Cheng, H., Lysko, P. G., Mckenna, P. J., Feuerstein, R., Gu, J., Lysko, K. A., Davis, L. L. & Feuerstein, G. (1992) *J. Pharmacol. Exp. Ther.,* 263, 92–98.

The antihypertensive action of carvedilol is mediated primarily by decreasing total peripheral vascular resistance without causing the concomitant reflex changes in heart rate commonly associated with other antihypertensive agents. Willette, R. N., et al. supra; Nichols, A. J., et al. supra; Ruffolo, R. R., Jr., Gellai, M., Hieble, J. P., Willette, R. N. & Nichols, A. J. (1990) *Eur. J. Clin. Pharmacol.,* 38, S82–S88. Carvedilol also markedly reduces infarct size in rat, canine and porcine models of acute myocardial infarction, Ruffolo, R. R., Jr., et al., *Drugs of Today,* supra, possibly as a consequence of its antioxidant action in attenuating oxygen free radical-initiated lipid peroxidation. Yue, T.-L., et al. supra.

Recently, I have discovered that the compounds of Formula I, particularly carvedilol, are able to block mitogen-stimulated proliferation of cultured rat aortic vascular smooth muscle cells in vitro. The most striking observation from these studies is that said compounds, particularly carvedilol, are able to block the proliferative actions of several pharmacologically unrelated mitogens, including thrombin, PDGF, epidermal growth factor (EGF), angiotensin II and endothelin-1, with an $IC_{50}$ of approximately 1 µM in the case of carvedilol. This is an action that is not shared by other β-adrenoceptor antagonists, such as labetalol, celiprolol or sotalol. Because said compounds, particularly carvedilol inhibit the proliferative actions of multiple mitogenic stimuli, the use of said compounds, particularly carvedilol, to inhibit the proliferation of smooth muscle cells, and therefore to prevent the therapeutically undesirable sequelae of such proliferation, they have a clear advantage over specific growth factor antagonists.

I have further discovered that the compounds of Formula I, particularly carvedilol, demonstrate superior protective effects against vascular smooth muscle proliferation in blood vessels. More particularly, the compounds of Formula I, including carvedilol, produce potent inhibition of vascular smooth muscle cell proliferation, migration, and neointimal proliferation in arteries subjected to acute injury induced by balloon angioplasty.

To that end, the present invention provides a use for a compound selected from the group consisting essentially of the compounds of Formula I, preferably carvedilol, or a pharmaceutically acceptable salt thereof, said use being for inhibition of proliferation and migration of smooth muscle cells in mammals, preferably human beings, particularly for preventing restenosis by angioplasty-induced neointimal proliferation in blood vessels of patients surviving PTCA; for inhibition of development of atherosclerosis; or for suppressing the progression of vascular hypertrophy associated with hypertension.

The present invention also provides a method of treatment for inhibition of proliferation and migration of smooth muscle cells in mammals, preferably human beings, particularly a method of treatment for preventing restenosis by angioplasty-induced neointimal proliferation in blood vessels of patients surviving PTCA; for inhibition of development of atherosclerosis; or for suppressing the progression of vascular hypertrophy associated with hypertension, said method comprising internally administering to a patient in need thereof an effective dose of a pharmaceutical composition comprising a compound according to claim 1, preferably carvedilol, or a pharmaceutically acceptable salt thereof.

As further illustrated in the Examples below, carvedilol affords profound protection (i.e., 84% reduction in intimal cross-sectional area) against balloon angioplasty-induced neointimal smooth muscle proliferation, migration and vascular stenosis in the rat common carotid artery model. In addition, carvedilol significantly inhibits vascular smooth muscle cell migration in vitro, and inhibits human vascular smooth muscle mitogenesis mediated by a wide variety of different mitogens, which, without being limited by any mechanistic explanation or theory of operation, accounts for the pronounced protection of vascular restenosis following balloon angioplasty in vivo.

The anti-proliferative protective mechanism of carvedilol according to the present invention is not the result of blockade of calcium channels or angiotensin II receptors, both of which have been implicated in the stenosis that results from balloon angioplasty, inasmuch as hemodynamic experiments demonstrated that the present dosing regimen of carvedilol does not produce significant effects on calcium channels or angiotensin II receptors. Furthermore, in a similar animal model to that employed in the present invention, the calcium channel blocker nifedipine produced less than 40% protection in the rabbit femoral artery following angioplasty. Jackson, C. L., Bush, R. C. & Bowyer, D. E. (1988) *Artheroscler,* 69, 115–122.

Although β-adrenoceptor blockade cannot be ruled out as a mechanism by which carvedilol protects against the vascular smooth muscle response to angioplasty, there is no evidence to suggest that these receptors are capable of mediating smooth muscle mitogenesis. In contrast, however, evidence does exist suggesting that $a_1$-adrenoceptor activation by circulating norepinephrine may be involved in luminal stenosis following angioplasty. However, the $a_1$-adrenoceptor antagonist, prazosin (1 mg/kg, p.o.), produces only 16% inhibition of the vascular smooth muscle proliferation observed following rat carotid artery angioplasty. Fingerle, J., et al., supra. Furthermore, it is not likely that the hypotensive actions of carvedilol contribute to the observed antiproliferative actions inasmuch as other antihypertensive agents lack the marked effects on vascular restenosis observed with carvedilol. In addition, continuous administration of the angiotensin II receptor antagonist losartan over a similar time period produced a similar reduction in systemic blood pressure to that observed with carvedilol in the rat model of the present invention, but only produced a 48% reduction in neointimal proliferation. Kauffman, R. F., et al., supra. Similarly, equal hypotensive doses of several other antihypertensive agents, such as minoxidil or hydralazine, failed to produce significant protection against vascular restenosis. Powell, J. S., Müller, R. K. M. & Baumgartner, H. R. (1991) *J. Am. Coll. Cardiol.,* 17, 137B–142B.

Chemotactic migration of medial smooth muscle cells into the intima is an important first step in the pathogenesis of neointima formation following balloon angioplasty. PDGF is believed to be a key substance for promoting smooth muscle cell migration and proliferation. Ferns, G. A. A., et al., supra; Ross, R. (1986) *N. Engl. J. Med.* 314 488–500. According to the present invention, carvedilol inhibits smooth muscle cell migration induced by PDGF with an $IC_{50}$ value comparable with the potencies observed for inhibiting smooth muscle proliferation and antioxidant activity. Without being limited by any mechanistic explanation or theory of operation, the ability of carvedilol to inhibit myointimal formation in vivo may in part be related to direct inhibition of the physical migration of vascular smooth muscle from the tunica media into the tunica intima, and also in part through antioxidant activity of carvedilol which may inhibit the recruitment of macrophages and monocytes to the injury site. Since oxidized low density lipoprotein (LDL) is also chemotactic in vascular smooth muscle, and carvedilol inhibits the oxidation of LDL, this could be an additional mechanism contributing to the marked inhibition of neointimal formation in vivo.

While the precise molecular events leading to the anti-proliferative and anti-migratory actions of carvedilol await further elucidation, the new medical use of carvedilol and method of treatment using carvedilol according to the present invention afford pronounced protection in an animal model of neointimal formation and stenosis following angioplasty. The degree of protection produced by carvedilol is only matched by the recent report of an experimental c-myb antisense oligonucleotide. Simons, M., Edelman, E. R., Dekeyser, J.-L., Langer, R. & Rosenberg, R. D. (1992) *Nature,* 359, 67–70. This was achieved only via the direct deposition of anti-sense construct onto the injured vascular surface in contrast to the present use and method of treatment in which the anti-stenotic effects are conveniently achieved using systemic administration which is more amenable to conventional medical practice. The extent of carvedilol-induced protection from restenosis (up to 84%) using a total daily dose of 2 mg/kg far exceeds that reported for other compounds in several animal models.

Compounds of Formula I may be conveniently prepared as described in U.S. Pat. No. 4,503,067. Carvedilol is commercially available from SmithKline Beecham Corporation (KREDEX®) and Boehringer Mannheim GmbH (Germany).

Pharmaceutical compositions of the compounds of Formula I, including carvedilol, may be administered to patients according to the present invention in any medically acceptable manner, preferably parenterally. For parenteral administration, the pharmaceutical composition will be in the form of a sterile injectable liquid stored in a suitable container such as an ampoule, or in the form of an aqueous or nonaqueous liquid suspension. The nature and composition of the pharmaceutical carrier, diluent or excipient will, of course, depend on the intended route of administration, for example whether by intravenous or intramuscular injection.

Pharmaceutical compositions of the compounds of Formula I for use according to the present invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinyl-pyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carder may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Dosing in humans for the treatment of disease according to the present invention should not exceed about 100 mg/day of the compounds of Formula I, including carvedilol. For prevention of reocclusion following PTCA, the preferred dosing regimen is administration of from about 12.5 mg/day to about 100 mg/day of a compound of Formula I, preferably carvedilol, in a single dose or multiple doses up to three times daily before, during, and for up to six months post-angioplasty; most preferably the dosage is about 25 mg/day 3 times daily. It will be appreciated that the actual preferred dosages of the compounds being used in the compositions of this invention will vary according to the particular composition formulated, the mode of administration, the particular site of administration, the host being treated, and the particular disease being treated.

No unacceptable toxicological effects are expected when the compounds of Formula I, including the compound of Formula II, are used according to the present invention.

In the following Examples, all temperatures are in degrees Centigrade (°C.). Unless otherwise indicated, all of the starting materials were obtained from commercial sources. Without further elaboration, it is believed that one skilled in the an can, using the preceding description, utilize the invention to its fullest extent. These Examples are given to illustrate the invention, not to limit its scope. Reference is made to the claims for what is reserved to the inventor hereunder.

EXAMPLES

Materials

Human epidermal growth factor and platelet-derived growth factor A/B were purchased from Boehringer Mannheim Corporation (Indianapolis, Ind.); [$^3$H]thymidine (specific activity=110 Ci/mmol; New England Nuclear, Boston, Mass.) and human thrombin was purchased from Sigma (St. Louis, Mo.). Carvedilol was obtained from Boehringer Mannheim (Germany). Solutions of carvedilol were prepared for injection immediately prior to each administration by dissolving 5 mg of compound in a vehicle that consisted of 0.3 ml of acid-ethanol (equal volumes of 100% ethanol and 1M HCl) in 4.7 ml of sterile distilled water. All other chemicals used were reagent grade from commercial sources and were used without further purification.

Statistics

Values are expressed as the mean ±S.E.M and n represents the number of animals or separate experiments studied in a particular group. Statistical comparisons were made using a one-way analysis of variance with a p value <0.05 accepted as significant.

Culture of Vascular Smooth Muscle Cells

Primary cultures of rat aortic vascular smooth muscle, for use in the migration studies, were prepared by an explant technique as described previously in Ohlstein, E. H., Arleth, A., Bryan, H., Elliott, J. D. & Sung, C.-P. (1992) *Eur. J. Pharmacol.*, 225, 347–350. Cryopreserved primary cultures of human pulmonary artery smooth muscle cells (passage 3), for use in the DNA synthesis studies, were obtained from Clonetics Corp. (San Diego, Calif.). Cells were grown in a modified MCDB 131 formulation containing 5 % fetal bovine serum, 10 ng/ml epidermal growth factor, 2 ng/ml basic-fibroblast growth factor, 1 µM dexamethasone, 10 µg/ml gentamicin sulfate, and 10 ng/ml amphotericin B (Clonetics Corp.).

DNA Synthesis

Human vascular smooth muscle cells were plated into 24 well plates (Corning, N.Y.) ($2\times10^4$ cells/cm$^2$, passage 6) and grown to confluence (3 days). Cells were then made quiescent ($G_o$) by substituting serum-containing medium with Dulbecco's modified Eagle's medium (DMEM; Gibco Laboratories, Grand Island, N.Y.) containing insulin (5 µg/ml), transferrin (5 µg/ml) and sodium selenite (5 ng/ml) for 48 hr. Cells were replenished with fresh medium once between and after the 48 hr quiescent period. Carvedilol was added 15 min prior to the addition of a mitogen for an additional 24 hr incubation. DNA synthesis was assessed by measuring the radioactivity incorporation (4 hr) of [$^3$H] thymidine into the TCA insoluble fraction.

EXAMPLE 1

Migration of Vascular Smooth Muscle

The procedure for assessing vascular smooth muscle cell migration was described previously in Hidaka, Y., Eda, T., Yonemoto, M. & Kamei, T. (1992) *Atheroscler.* 95, 87–94. Briefly, rat aortic vascular smooth muscle cells (passage 3) were suspended ($1\times10^6$ cells/ml) in serum free DMEM supplemented with 0.2% (w/v) bovine serum albumin (Sigma). Migration assays were performed in modified Boyden chambers using Transwell (Costar, Cambridge, Mass.) cell culture chambers with a polycarbonate 8 µm pore size membrane. PDGF was dissolved in DMEM and placed in the lower compartment in the presence, or absence, of carvedilol. Vascular smooth muscle cells ($5\times10^5$ cells) were then loaded in the upper compartment and incubated for 24 hr at 37° C. in a humidified atmosphere containing 5% $CO_2$. Non-migrated cells on the upper surface were scraped away gently and washed three times with PBS. Filters were fixed in methanol and stained with Giemsa. The number of vascular smooth muscle cells per 100×high power field (HPF) that had migrated to the lower surface of the filters was determined microscopically. Four HPFs were counted per filter. Experiments were performed either in duplicate or triplicate.

PDGF produced concentration-dependent increases in the migration of rat vascular smooth muscle cells with a maximal effect obtained at a concentration of 1 nM. When carvedilol was placed in the lower chamber with PDGF, the migration response was inhibited significantly in a concentration-dependent manner with an $IC_{50}$ value for carvedilol of 3 μM.

EXAMPLE 2

Balloon Angioplasty of Rat Carotid Arteries

The animals used in this study were divided into two groups, (a) those used for hemodynamic studies and (b) those used for histopathological examination of the degree of neointimal proliferation following carotid artery balloon angioplasty. These two major groups were further subdivided into animals that were treated with carvedilol (1 mg/kg, i.p., twice daily; approximately 5 μmol/kg/day) and those that served as controls (which received an equal volume of carvedilol vehicle). All animals were pretreated with either carvedilol or vehicle three days prior to commencing either the hemodynamic studies or carotid artery angioplasty (the latter group receiving carvedilol or vehicle for the subsequent 14 days after surgery, at which time the animals were sacrificed for the histological processing of the carotid arteries).

Left common carotid artery balloon angioplasty was performed under aseptic conditions in anesthetized (sodium pentobarbital; 65 mg/kg, i.p.) male Sprague-Dawley rats (380–420 g) that had been pretreated for 3 days with either carvedilol or vehicle. Following an anterior midline incision, the left external carotid artery was identified and cleared of adherent tissue back to its point of origin at the common carotid artery bifurcation. Special care was taken to avoid crush injury to the vagus or the associated superior cervical ganglion and sympathetic cord while clearing the distal portion of the carotid artery. A 2-F Fogarty arterial embolectomy catheter (Baxter Healthcare Corporation, Santa Ana, Calif.) was inserted into the lumen of the left external carotid artery and guided a fixed distance (5 cm) down the external carotid and common carotid arteries to a point such that the tip of the catheter was proximal to the aortic arch. Once in position, the balloon was inflated with fluid sufficient to generate slight resistance with the vessel wall when the catheter was withdrawn. With the balloon inflated, the catheter was then withdrawn at a constant rate (approximately 2 cm/sec) back to a point proximal to the site of insertion in the external carotid artery. This procedure was performed a total of three times, then the catheter was removed and the wound was closed. Animals were housed in Plexiglas cages in pairs under a 12 hr light/dark cycle with access to standard laboratory chow and drinking water ad libitum.

Common carotid arteries were removed from rats 14 days after they had undergone balloon angioplasty for use in histopathological studies. The extent of neointima formation evident on day 14 was quantified histologically. Vessels were perfusion fixed under constant pressure (95–100 mmHg) in situ immediately following sodium pentobarbital overdose. The entire length of the common carotid artery, extending from the aortic arch to the carotid artery bifurcation (approximately 5 cm in length), was removed for histological processing. Arterial cross sections (8 μm) were cut from paraffin blocks containing the middle third of these arteries and were processed for hematoxylin and eosin staining. The cross-sectional areas of the blood vessel layers (intima, media and adventitia) were quantified using a Bioscan Optimus (Edmonds, Wash.) cell imaging system.

All experiments were performed specifically in accordance with the guidelines of the Animal Care and Use Committee, SmithKline Beecham Pharmaceuticals and AALAC.

Carvedilol treatment had no effect on the increases in body weight over the 17 day treatment period (380±6 g, n=9, and 377±6 g, n=10, in carvedilol- and vehicle-treated groups 3 days prior to surgery and 425±9 g and 416±7 g 14 days after balloon angioplasty, respectively). Rats treated with carvedilol (1 mg/kg. i.p.; twice daily for three days) had significantly lower resting mean arterial blood pressures and heart rates (102±5 mmHg and 305±9 bpm, respectively; n=6) than those recorded in the vehicle-treated group (125±3 mmHg and 360±21 bpm, respectively; n=7).

Balloon angioplasty of the left common carotid artery produced marked intimal thickening in vehicle-treated rats resulting in a highly significant, 20-fold increase in the intima:media ratio. The contralateral right common carotid arteries that were not subjected to the angioplasty procedure were normal in both carvedilol- and vehicle-treated rats; i.e., no differences were observed between the intimal, medial and adventitial areas, and these vessels had identical intima:media ratios. The extent of neointimal formation in the carotid arteries subjected to angioplasty was profoundly attenuated by carvedilol treatment which caused an 84% decrease in intimal cross-sectional area, and a comparable 81% decrease in the intima:media ratio. Carvedilol treatment did not alter either medial or adventitial cross-sectional area. Thus, carvedilol treatment afforded marked, and highly significant, protection from the myointimal proliferation and migration that results from vascular wall injury following balloon angioplasty.

EXAMPLE 3

Inhibition of Human Vascular Smooth Muscle Mitogenesis

Carvedilol (0.1–10 μM) produced a concentration-dependent inhibition of mitogenesis stimulated by PDGF (1 nM), EGF (1 nM), thrombin (0.1 U/ml) and fetal bovine serum (1%) in cultured human pulmonary artery smooth muscle cells. The $IC_{50}$ values for carvedilol against mitogenesis stimulated by the growth factors and serum were between 0.3 and 2 μM. This effect was fully reversible, as cells regained full responsiveness to growth stimulation if carvedilol was washed out of the medium following 24 hr incubation.

The above description fully discloses how to make and use the present invention. However, the present invention is not limited to the particular embodiment described hereinabove, but includes all modifications thereof within the scope of the following claims.

We claim:

1. A method of treating atherosclerosis in human patients, comprising internally administering to a patient in need thereof an effective dose of a pharmaceutical composition comprising a compound of Formula I:

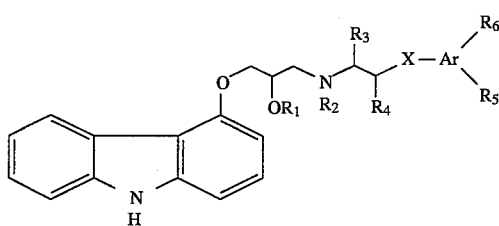

wherein:

R₁ is hydrogen, lower alkanoyl of up to 6 carbon atoms or aroyl selected from benzoyl and naphthoyl;

R₂ is hydrogen, lower alkyl of up to 6 carbon atoms or arylalkyl selected from benzyl, phenylethyl and phenylpropyl;

R₃ is hydrogen or lower alkyl of up to 6 carbon atoms;

R₄ is hydrogen or lower alkyl of up to 6 carbon atoms, or when X is oxygen, R₄ together with R₅ can represent —CH₂—O—;

X is a valency bond, —CH₂, oxygen or sulfur;

Ar is selected from phenyl, naphthyl, indanyl and tetrahydronaphthyl;

R₅ and R₆ are individually selected from hydrogen, fluorine, chlorine, bromine, hydroxyl, lower alkyl of up to 6 carbon atoms, a —CONH₂—group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms;

or a pharmaceutically acceptable salt thereof.

2. A method of treatment according to claim 1 wherein said pharmaceutical composition is suitable for parenteral administration.

3. A method of treatment according to claim 1 wherein said compound is carvedilol.

* * * * *